US00PP27839P2

(12) United States Plant Patent
Hansen

(10) Patent No.: US PP27,839 P2
(45) Date of Patent: Apr. 4, 2017

(54) ***HIBISCUS* PLANT NAMED 'VINTAGE WINE'**

(50) Latin Name: ***Hibiscus* hybrid (L.)**
Varietal Denomination: Vintage Wine

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 82 days.

(21) Appl. No.: 14/756,231

(22) Filed: Aug. 19, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Anne Grunberg

(57) ABSTRACT

A new and distinct cultivar of hardy herbaceous perennial *Hibiscus* hybrid plant named 'Vintage Wine' comprising an overall upright dense branching, numerous dark scarlet-red flowers with overlapping petals and a darker red lustrous eye. The foliage is dark-green, primarily ovate with slight blushing of greyed-purple.

1 Drawing Sheet

Botanical classification: *Hibiscus* hybrid (L.).
Variety denomination: 'Vintage Wine'.

BACKGROUND AND ORIGIN OF THE PLANT

The present invention relates to the new and distinct hardy, herbaceous, *hibiscus* plant, *Hibiscus* 'Vintage Wine' hybridized by the inventor on Aug. 2, 2011 at a nursery in Zeeland, Mich. The new plant, originally labeled # 11-82-01, is a single seedling selection from a cross between *Hibiscus* 'Cranberry Crush' U.S. Plant Pat. No. 21,984 (female pod parent) times *Hibiscus* 'Midnight Marvel' U.S. Plant Pat. No. 24,079 (male pollen parent). The seed was harvested on Oct. 13, 2011 the specific seedling passed the initial trial in the summer of 2012. Both parents have a complex mixture of species in them, most likely including the species: *moscheutos* and *coccineus*. *Hibiscus* 'Vintage Wine' was first asexually propagated in 2013 by both stem tip cuttings and sterile tissue culture at the same nursery in Zeeland, Mich. The resultant asexually propagated plants have been found to be stable and true to type in successive generations of asexual reproduction using both systems.

BRIEF SUMMARY OF THE PLANT

*Hibiscus* 'Vintage Wine' differs from its parents as well as all other hardy herbaceous *hibiscus* known to the applicant in many traits. The foliage color of 'Plum Fantasy' is dark green with generally tri-lobed foliage. The most similar *hibiscus* in flower color known to the applicant is the male parent, 'Midnight Marvel' U.S. Plant Pat. No. 24,079. Other similar cultivars include: 'Carafe Yobordeaux' U.S. Plant Pat. No. 17,638, 'Cherry Brandy' U.S. Plant Pat. No. 18,944, 'Cinnamon Grappa' U.S. Plant Pat. No. 18,964, 'Heartthrob' U.S. Plant Pat. No. 24,760, 'Midnight Marvel' U.S. Plant Pat. No. 24,079 and 'Mars Madness' (co-pending U.S. Plant patent application Ser. No. 14/756,234). In comparison, 'Midnight Marvel' has a more cupped flower shape, more orange-red tinting of the petals, and is shorter in habit than the new plant. 'Heartthrob' has a darker purple-red flower color with darker buds and is narrower and more open in habit. 'Mars Madness' is slightly lighter purple-red in flower color, and has a more green ovate leaf shape and more open habit. Compared to the female parent select, 'Cranberry Crush', the new plant has a taller, more upright dense habit with flatter flower face, darker scarlet color, and more ovate leaf shape.

Table 1 below gives an outline comparison of these other comparison cultivars.

TABLE 1

| CULTIVAR | Leaf color | leaf shape | Flower color |
|---|---|---|---|
| 'Carafe Yobordeaux' | dark green | cordate to ovate | red purple |
| 'Cherry Brandy' | green with some purple tinting | palmate | dark red |
| 'Cinnamon Grappa' | green | palmate | red-purple |
| 'Cranberry Crush' | dark green with purple overtones | ovate to tri-lobed | deep scarlet red |
| 'Heartthrob' | dark green | ovate to cordate | dark greyed-purple, blackish red eye |
| 'Mars Madness' | dark-green, coppery-purple | tri-lobed | cherry red, darker halo eye and veins |
| 'Midnight Marvel' | dark green, purple overlay | palmate | deep scarlet red, darker eye |
| 'Vintage Wine' | dark green | ovate to cordate | dark scarlet red, darker eye |

| CULTIVAR | Habit | Size (H × W) |
|---|---|---|
| 'Carafe Yobordeaux' | upright outward | 140 cm × 120 cm |
| 'Cherry Brandy' | upright outward | 140 cm × 120 cm |
| 'Cinnamon | upright outward | 140 cm × 120 cm |
| 'Cranberry Crush' | mound | 100 cm × 90 cm |
| 'Heartthrob' | rounded mound | 100 cm × 140 cm |
| 'Mars Madness' | broad mound | 135 cm × 180 cm |
| 'Midnight Marvel' | mound | 85 cm × 80 cm |
| 'Vintage Wine' | upright mound | 135 cm × 150 cm |

*Hibiscus* 'Vintage Wine' is a unique hardy herbaceous *hibiscus* with the following combined traits:

1. Hardy perennial with dense branching and overall upright habit.

2. Many flowers over a prolonged season having dark scarlet-red overlapping petals, darker red lustrous eye and dark buds.
3. Dark-green, heavily-dissected primarily ovate foliage with blushing of greyed-purple.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
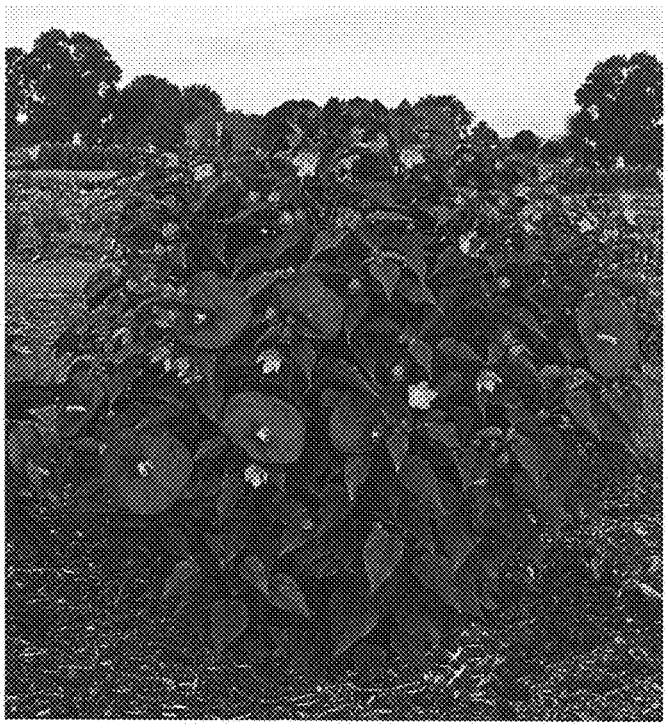
FIG. 1 shows a three-year old plant in the landscape.
Figure 2:
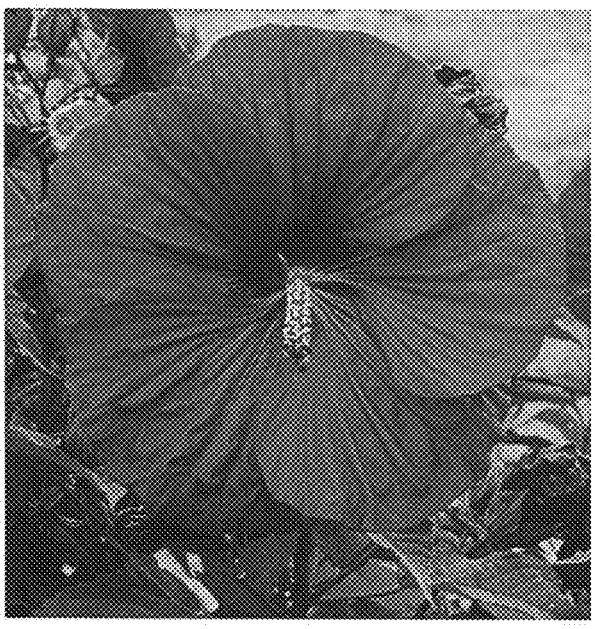
FIG. 2 shows a close-up of the flowers with puckered petals of dark scarlet-red.

The following descriptions and color references are based on the 2001 edition of The Royal Horticultural Society Colour Chart except where common dictionary terms are used. The new plant, *Hibiscus* 'Vintage Wine', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full-sun trials of a nursery in Zeeland, Mich. with supplemental fertilizer and water as needed. The plants are natural habit and were not treated with plant growth regulators, nor were they pinched at any time in the growth year.

Parentage: *Hibiscus* 'Cranberry Crush' U.S. Plant Pat. No. 21,984 (female seed parent) times 'Midnight Marvel' U.S. Plant Pat. No. 24,079 (male pollen parent).

Propagation:

*Method*.—Stem cuttings and sterile plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant shape and habit*.—Hardy herbaceous perennial with about 17 to 33 thick upright and heavily branched main stems producing a upright spreading mound about 135.0 cm tall and about 150.0 cm wide, widest about 90 cm above soil line; about 12 to 18 primary branches per main stem protruding at about 50° to 45° angle from horizontal, branches on the middle third of the main stem node; primary branch size: between about 27.0 cm and about 8.0 cm long (shorter at the upper nodes) and average 4.5 mm diameter at the base of branch; flowering on the upper ⅓ of the plant beginning at axillary nodes while still developing at the apex.

*Stem*.—Rounded, glabrous, glaucous; average 120.0 cm tall and 3.0 cm diameter at base.

*Stem color*.—Between RHS 146C in sunlight protected area and RHS 183A in more light.

*Internode*.—About 44 nodes per stem, average internode length about 3.0 cm of unpinched plant, varied between 2.0 to 4.0 cm, greatest in middle portion of stem.

Foliage description: Alternate; dentate; glabrous; mostly deeply ovate, rarely tri-lobed or shallowly dissected; texture above lustrous in young distal leaves and matte in proximal leaves, texture below matte; leaf blade size to about 16.0 cm long and 11.0 cm across, average 14.0 cm long and 8.0 cm wide, becoming smaller in distal portion of stem.

*Foliage color*.—Young adaxial nearest RHS 139B, mature leaves nearest RHS 137A with a slight tint of RHS N187A or RHS 187B; abaxial side between RHS 146B and RHS 147B.

*Veins*.—Palmate; adaxial slightly impressed, abaxial ridged and rounded.

*Vein color*.—Primary and secondary adaxial veins mostly nearest RHS 183C, with less sun exposure nearest RHS 146D; primary and secondary abaxial veins nearest RHS 145C with some developing faint tinting of nearest RHS 183D.

*Petioles*.—Average size 8.5 cm long and 4.0 mm wide; mostly cylindrical with flattening at base; slightly glaucous; slightly puberulent.

*Petiole color*.—Adaxial nearest RHS 144A with tinting of nearest RHS 178B; and abaxial between RHS 145A and RHS 146D with less tinting than adaxial nearest RHS 182A.

Flower description:

*Buds*.—One day prior to opening about 6.5 cm long and 4.5 cm in diameter, bluntly apex and rounded base, unopened petals wrinkled at veins; prior to showing petals about buds are about 3.7 cm long and about 2.6 cm in diameter, ovoid with acute apex, carinate at the sepal fusion seams.

*Bud color*.—Exposed petals between RHS N186C and RHS 187B; prior to showing petals bud color between RHS 144D and RHS 146D rarely with different colored veining; sepal carina having light tinting nearest RHS N183C.

*Epicalyx*.—Entire; smooth; puberulent abaxial and adaxial; linear with sharply acute apex and attenuate base, curved around sepals; typically 11 to 12 per flower; about 2.0 cm long tapering to base of about 2.0 mm wide; adaxial and abaxial color nearest RHS 146A with tinting of nearest RHS 187A in high sunlight exposure.

*Sepals*.—Five; proximal half connate forming campanulate star-shaped calyx; acute apex; margin entire, edentate; minutely puberulent; individually about 3.8 cm long and 2.2 cm wide at fusion point; combined about 6.5 cm across and 2.5 cm deep.

*Sepal color*.—Abaxial between RHS 146B and RHS 143A, adaxial color between RHS 144B and RHS 145B.

*Flowers*.—Solitary, 28 to 34 per main stem without pinching; predominately flat-faced; mostly outwardly facing; average 21.0 cm across and 6.0 cm deep from outside face to edge of reflexed petals, larger in early part of flowering season; persist for a one to two days; effective for at least 9 weeks beginning early August and lasting into October; no detectable fragrance.

*Petals*.—Five; glabrous, slightly lustrous in center, dull both adaxial and abaxial toward middle and apex, adnate to the androecium to form a column, imbricate to about 80% overlapping at widest part (petals 80% overlapping the next petals on either side), palmately veined, primary and secondary veins impressed on front and ribbed on back; shape: rounded; margins: entire, edentate; apex: rounded; base: short claw-like; size: average 11.0 cm long and 12.0 cm wide at widest portion (larger in earlier part of flowering season); center dark eye about 5.0 cm diameter.

*Petal color*.—Adaxial between RHS 187C and RHS 187B with a lustrous darker eye between RHS 187A and RHS 187B; abaxial color between RHS 187C and RHS 187B; adaxial vein color between RHS 187C and RHS 187B, abaxial vein color nearest RHS 60A.

*Gynoecium*.—Style: enclosed in column about 6.0 cm long and 1.0 cm wide at base; column color nearest RHS 60A distally and between RHS 61B and RHS 60D toward middle and base; style protruding from column and split in distal about 9.0 mm portion into typically five branches and protrudes from column, branch diameter about 1.0 mm; branch color between RHS 187C and RHS 187B; Stigma: typically five; globose, puberulose, about 3.0 mm in diameter, nearest RHS 187B; Ovary: superior, about 11.0 mm across at base and about 9.0 mm tall; bluntly acute apex; color between RHS 145B and RHS 145C.

*Androecium*.—Filaments: numerous, about 90; less than 1.0 mm in diameter and about 4.0 mm long; attached along nearly the entire length of column; color between RHS 11C and RHS 11D along sides and tinted with nearest RHS 61D; Anthers: reniform; about 2 mm long and about 1 mm wide; color nearest RHS 186B; Pollen: abundant, globose, less than 0.1mm long, nearest RHS 16B.

*Pedicel*.—Rounded in cross section; glaucous; puberulent; length from base of sepal to abscission point average about 1.5 cm long and about 4.0 mm wide, longer on early flowers and decreasing in distal flowers.

*Pedicel color*.—Between RHS 144A and RHS 146C toward flower base and developing tinting of nearest RHS 183D.

*Peduncle*.—Rounded, glabrous, puberulent; average about 5.0 cm long from abscission point to node of main stem and about 3.0 mm wide at base, longer on earlier flowers.

*Peduncle color*.—Nearest RHS 144A with tinting of RHS 186A in higher direct sun exposure.

*Fruit*.—Few, loculicidal capsule; glabrous; globose, occasionally with abruptly acute apex; color between RHS N199B and RHS N199C when mature.

*Seed*.—Minutely floccose, typically globose; about 3.0 mm in diameter; color between RHS 200A and RHS N199B.

Resistance: The plant grows best with plenty of moisture, but is able to tolerate some drought once established. Other pest and disease resistance beyond that of other hardy perennial *hibiscus* cultivars has not been observed.

Hardiness at least from USDA zone 4 through 9.

I claim:

1. A new cultivar of hardy herbaceous perennial *Hibiscus* hybrid plant named 'Vintage Wine' as herein illustrated and described, suitable for potted plant culture, landscaping as a specimen or en masse, and especially suited for patios and confined spaces because of the compact habit.

* * * * *